US009474826B2

(12) United States Patent
Yoshida et al.

(10) Patent No.: US 9,474,826 B2
(45) Date of Patent: Oct. 25, 2016

(54) KIT FOR ADHERING BIOLOGICAL HARD TISSUES

(71) Applicants: NATIONAL UNIVERSITY CORPORATION OKAYAMA UNIVERSITY, Okayama-shi (JP); JUNSEI EDUCATIONAL INSTITUTION, Takahashi-shi (JP)

(72) Inventors: Yasuhiro Yoshida, Sapporo (JP); Masato Tanaka, Okayama (JP); Kazuomi Suzuki, Okayama (JP); Toshifumi Ozaki, Okayama (JP); Tomohiro Takahata, Marugame (JP); Masao Irie, Okayama (JP); Mariko Nakamura, Takahashi (JP); Mitsunobu Kawashima, Tainai (JP); Yamato Nojiri, Tainai (JP); Koichi Okada, Koutou-ku (JP); Masahiro Nagao, Nishinomiya (JP)

(73) Assignees: National University Corporation Okayama University, Okayama-shi (JP); Junsei Educational Institution, Takahashi-shi (JP)

( * ) Notice: Subject to any disclaimer, the term of this patent is extended or adjusted under 35 U.S.C. 154(b) by 0 days.

(21) Appl. No.: 14/879,620

(22) Filed: Oct. 9, 2015

(65) Prior Publication Data
US 2016/0030627 A1 Feb. 4, 2016

Related U.S. Application Data

(63) Continuation of application No. 13/580,573, filed as application No. PCT/JP2011/053838 on Feb. 22, 2011, now Pat. No. 9,186,433.

(30) Foreign Application Priority Data

Feb. 22, 2010 (JP) .................................. 2010-036350

(51) Int. Cl.
*A61K 6/00* (2006.01)
*A61L 24/02* (2006.01)
*A61L 24/08* (2006.01)
*A61L 26/00* (2006.01)
*A61L 27/00* (2006.01)

(52) U.S. Cl.
CPC .............. *A61L 24/08* (2013.01); *A61K 6/0023* (2013.01); *A61L 24/02* (2013.01); *A61L 26/00* (2013.01); *A61L 27/00* (2013.01); *A61L 2430/02* (2013.01)

(58) Field of Classification Search
CPC ..... A61K 6/0023; A61L 26/00; A61L 27/00; C08K 5/00
USPC .................................................. 514/769, 777
See application file for complete search history.

(56) References Cited

U.S. PATENT DOCUMENTS

| 5,449,508 | A | 9/1995 | Unger |
| 5,522,893 | A | 6/1996 | Chow et al. |
| 5,542,973 | A | 8/1996 | Chow et al. |
| 5,545,254 | A | 8/1996 | Chow et al. |
| 5,695,729 | A | 12/1997 | Chow et al. |
| 5,861,048 | A | 1/1999 | Kamasaka et al. |
| 6,206,957 | B1* | 3/2001 | Driessens ............... A61L 24/02 106/35 |
| 6,268,182 | B1 | 7/2001 | Kamasaka et al. |
| 6,325,992 | B1 | 12/2001 | Chow et al. |
| 8,147,807 | B2* | 4/2012 | Yoshida .................... A61K 8/73 424/49 |
| 8,999,298 | B2* | 4/2015 | Yoshida ................... A61K 8/24 424/57 |
| 9,186,433 | B2* | 11/2015 | Yoshida ............... A61K 6/0023 |
| 2008/0038210 | A1* | 2/2008 | Yano ........................ A61K 8/24 424/49 |
| 2008/0171002 | A1 | 7/2008 | Tuduri et al. |
| 2009/0202610 | A1* | 8/2009 | Wilson .................. A61L 31/022 424/426 |
| 2009/0280156 | A1 | 11/2009 | Hotokebuchi et al. |
| 2010/0210714 | A1 | 8/2010 | Lee et al. |
| 2010/0330005 | A1 | 12/2010 | Yoshida et al. |
| JP | 6-321515 | | 11/1994 |
| JP | 7-35281 | | 4/1995 |

FOREIGN PATENT DOCUMENTS

| EP | 0 329 098 | | 8/1989 |
| EP | 0 719 783 A2 | | 7/1996 |
| EP | 0 719 783 A3 | | 7/1996 |

(Continued)

OTHER PUBLICATIONS

The Merck Manual, 1992, 16th Ed., pp. 1352-1353 and 2491.*

(Continued)

*Primary Examiner* — Ganapathy Krishnan
(74) *Attorney, Agent, or Firm* — Oblon, McClelland, Maier & Neustadt, L.L.P.

(57) ABSTRACT

A kit for bonding to biological hard tissues, containing a phosphorylated polysaccharide, a polyvalent metal salt other than phosphates, and a solvent. The adhesive composition for biological hard tissues provided by the kit for bonding to biological hard tissues is suitably used in for medical uses, such as cement for bones or dental cement. In addition, since the adhesive composition has excellent bio-absorbability, it is useful as fusion materials for artificial joint prosthesis, fusion materials for spine fracture, fusion materials for extremity fracture, filling materials for bone tumors in the region of orthopedics, filling materials and restorative materials at dental caries-defective sites, luting materials for prosthetic restorative materials such as inlay and crown, pulp-capping and lining materials, implant surface treatment materials, periodontal disease therapeutic materials, hyperesthesia preventive materials, dental pulp capping materials, substrates for DDS, substrates for systems engineering, and tissue bonding materials in the dental region.

20 Claims, 8 Drawing Sheets

(56) References Cited

FOREIGN PATENT DOCUMENTS

| JP | 3017536 | 3/2000 | | |
|---|---|---|---|---|
| JP | 2005 34333 | 2/2005 | | |
| JP | 2005-330269 | 12/2005 | | |
| JP | 2006 150431 | 6/2006 | | |
| JP | 2007 6978 | 1/2007 | | |
| JP | 2009 7263 | 1/2009 | | |
| WO | 2008 010517 | 1/2008 | | |
| WO | WO 2008/010517 | * | 1/2008 | ............... A61K 8/60 |
| WO | 2008 029612 | 3/2008 | | |
| WO | 2009 091001 | 7/2009 | | |

OTHER PUBLICATIONS

Nakagawa, M., et al., "Osteointegration of titanium implant with CaCl_2 hydrothermal treatment," The Journal of the Japanese Society for Dental Materials and Devices, vol. 24, No. 5, p. 352, (2005) (with English translation).

Nakagawa, M., et al., "Initial attachment and proliferation of osteoblast-like cell on the high corrosion resistance titanium alloys hydrothermally treated with CaCl_2," The Journal of the Japanese Society for Dental Materials and Devices, vol. 23, No. 5, p. 408, (2004) (with English translation).

Yoshida, Y., et al., "Antibacterial Coating for Prevention of Caries and Periodontal Disease," Journal of the Japanese Association for Dental Science, vol. 28, pp. 39-43, (2009) (with English translation).

Watanabe, O., et al., "Analysis of action mechanisms of enhanced calcium absorption by phosphorylated polysaccharides," Journal of the Japanese Society of Nutrition, and Food Sience Sokai Koen Yoshishu, vol. 53, p. 197, (1999) (with English translation).

International Search Report Issued May 31, 2011 in PCT/JP11/53838 Filed Feb. 22, 2011.

Extended Search Report issued Jul. 28, 2014 in European Patent Application No. 11744816.7.

P.L. Granja, et al., "Cellulose Phosphates as Biomaterials. Mineralization of Chemically Modified Regenerated Cellulose Hydrogels", Journal of Materials Science, vol. 36, 2001, XP002726805, pp. 2163-2172.

P.L. Granja, et al., "Cellulose Phosphates as Biomaterials. I. Synthesis and Characterization of Highly Phosphorylated Cellulose Gels", Journal of Applied Polymer Science, vol. 82, 2001, XP02726806, pp. 3341-3353.

The Merck Manual, 1992, $16^{th}$ Ed., pp. 1352-1353 and p. 2491.

Mineral Data Publishing, version 1, 2005, p. 1.

NY/NJ Mineral Show, 1997, pp. 1-4.

Winentrance.com, 2000, pp. 1-2.

* cited by examiner

Example 1

Example 1 +
Commercially Available Resin

KIT FOR ADHERING BIOLOGICAL HARD TISSUES

This is a continuation of application Ser. No. 13/580,573, filed Aug. 22, 2012, which is the National Stage of International application no. PCT/JP2011/053838, filed Feb. 22, 2011, which claimed priority to Japanese patent application no. 2010-036350, filed Feb. 22, 2010, of which all of the disclosures are incorporated herein by reference in their entireties.

TECHNICAL FIELD

The present invention relates to a kit for bonding to biological hard tissues. More specifically, the present invention relates to a kit capable of providing an adhesive composition for biological hard tissues useful as, for example, bone cement, dental cement or the like, because the composition has excellent biocompatibility, and at the same time gives a cured product that is hardened with a sufficiently high strength, and further has strong adhesion to bones, tooth tissues, metals, or ceramics.

BACKGROUND ART

Hydroxyapatite $[Ca_{10}(PO_4)_6(OH)_2]$, obtainable by sintering a calcium phosphate composition, has a composition nearly the same as inorganic components such as bones or teeth, and has a bioactivity that is capable of being directly combined with tooth tissues so that the hydroxyapatite has been utilized as restorative materials for bone-defect parts or bone-gap parts. However, while a material made of the hydroxyapatite as mentioned above has excellent biocompatibility, the material may have difficulty in moldability in some cases in order to apply the material to a site having a complicated shape.

On the other hand, among the calcium phosphate compositions, it is known that a calcium phosphate composition of cement type, in other words, the composition having curability, gradually converts to hydroxyapatite in a live body or oral cavity, thereby making it possible to integrate with the biological hard tissues while keeping its form. The calcium phosphate composition as described above has not only excellent biocompatibility but also moldability, so that the application of the composition to a site having complicated shape is facilitated.

For example, Patent Publication 1 describes that a mixture of tetracalcium phosphate and dicalcium phosphate anhydrous is rapidly auto-cured in the presence of water, thereby forming hydroxyapatite having excellent mechanical strength.

PRIOR ART PUBLICATIONS

Patent Publications

Patent Publication 1: Japanese Patent Gazette No. 3,017,536

SUMMARY OF THE INVENTION

Problems to be Solved by the Invention

However, conventional calcium phosphate compositions have caused various problems in clinical sites, such as mechanical strength after curing is not sufficient, the adhesive property is low, so that holding strength in the fusion of a treatment site (fusion between bone and bone, or between bone and screw for fusion) is not sufficient, and the like. In view of these matters, a material showing excellent biocompatibility and at the same time giving a cured product that is hardened a sufficiently high strength, and further showing strong adhesion to bone, tooth tissues, a metal or ceramics is earnestly desired.

In addition, since the restorative materials for bone-defective sites and bone-gapped sites are subjected to osteogenesis by replacing the materials with the bone, it is desired that the restorative materials have bio-absorbability. However, the hydroxyapatite obtainable by conventional techniques has low absorbability, so that improvements are earnestly desired even in this aspect.

An object of the present invention is to provide a kit for bonding to biological hard tissues which is capable of providing an adhesive composition for biological hard tissues, giving a cured product that is hardened a sufficiently high strength, and having strong adhesion to bone, tooth tissues, a metal, or ceramics, and at the same time having excellent biocompatibility and bio-absorbability, and further having excellent agent-releasing property in a case where the agent having bioactivity is contained.

Means to Solve the Problems

In view of the above, as a result of intensive studies in order to solve the above-mentioned problems, the present inventors have found that a composition obtained from an aqueous solution containing a phosphorylated polysaccharide and a calcium salt gives a cured product that is hardened a sufficiently high strength, and also shows strong adhesion to bones, tooth tissues, metals or ceramics, and at the same time has excellent biocompatibility and bio-absorbability, and further has, in a case where the composition contains an agent having bioactivity, excellent agent-releasing property. The present invention has been perfected thereby.

Specifically, the present invention relates to a kit for bonding to biological hard tissues, containing a phosphorylated polysaccharide, a polyvalent metal salt other than phosphates, and a solvent.

Effects of the Invention

The kit for bonding to biological hard tissues of the present invention exhibits some excellent effects that the kit is capable of providing an adhesive composition for biological hard tissues, giving a cured product that is hardened a sufficient high strength, and showing strong adhesion to bones, tooth tissues, metals or ceramics, and at the same time having excellent biocompatibility and bio-absorbability, and further, in a case where the composition contains an agent having bioactivity, having excellent agent sustained-release property. Therefore, the adhesive composition for biological hard tissues provided by the kit for bonding to biological hard tissues of the present invention is suitable in materials for medical uses, such as cement for bones or dental cement. In addition, since the adhesive composition has excellent bio-absorbability, it is useful as fusion materials for artificial joint prosthesis, fusion materials for spine fracture, fusion materials for extremity fracture, filling materials for bone tumors in the region of orthopedics, filling material and restorative materials at dental caries-defective sites, luting materials for prosthetic restorative materials such as inlay and crown, pulp-capping and lining materials, implant surface treatment materials, periodontal disease therapeutic materials, hyperesthesia preventive materials,

MODES FOR CARRYING OUT THE INVENTION

Figure 1:
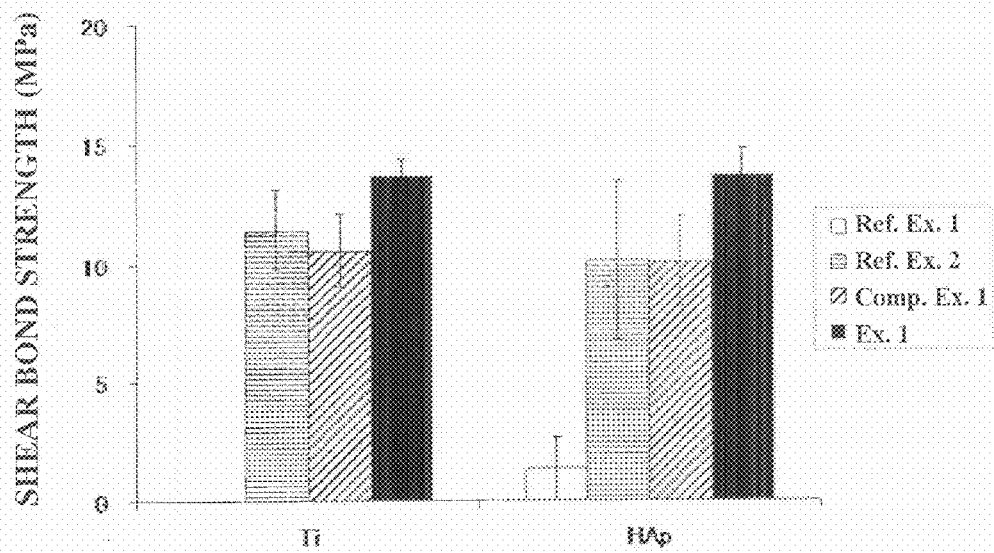
FIG. 1 is a graph showing the results of shear bond strength of the compositions of Example 1, Comparative Example 1, and Reference Examples 1 to 2.

The kit for bonding to biological hard tissues of the present invention has a great feature in that the kit contains a phosphorylated polysaccharide and a polyvalent metal salt other than phosphates, not the calcium phosphates themselves, as a composition similar to apatite largely contained in bones, teeth, and the like. Here, in the present specification, the biological hard tissues mean biological tissues such as bones, teeth, and tissues containing those.

Some of conventional adhesive compositions exhibit bonding property by polymerizing a polymerizable monomer such as PMMA (poly(methyl methacrylate)) or MMA (methyl methacrylate). However, the polymers have some disadvantages such that the bone loosening with the polymers takes place because the polymers have a low binding ability with bones and the like, and that heat generation during the polymerization and unreacted monomers and the like cause bad influences to live bodies. Also, there are some compositions containing calcium phosphates, but the compositions are not yet sufficient in the aspect of adhesive strength and productivity. In view of the above, as a result of studies, the present inventors have surprisingly found that when a phosphorylated polysaccharide and a polyvalent metal salt other than phosphates are combined, curing is progressed at a high reactivity, so that the cured product obtained has excellent bonding property to bones and metals, and also has high strength. In addition, when applied to bones and the like, it is found that the absorbability thereof is high, and that the composition is favorably replaced with the bones. Although the detailed reasons for such phenomena are not clarified, it is deduced from the fact that strong bonding property is exhibited because crosslinking or a curing reaction is quickly progressed by ion crosslinking between the phosphorylated polysaccharide and the polyvalent metal ions, and further that the polysaccharides forming a matrix for the cured product (gel) obtained contains a phosphate group.

The kit for bonding to biological hard tissues of the present invention contains a phosphorylated polysaccharide (A), a polyvalent metal salt (B), and a solvent (C).

The phosphorylated polysaccharide has low irritation and high compatibility to the biological tissues, and shows bio-absorbability. In addition, the phosphorylated polysaccharide dissolves apatite, in which a phosphate group or phosphate groups are a constituting inorganic component of the biological hard tissues, thereby releasing a part of calcium, a constituting element of apatite in the form of ions. Moreover, the phosphate group of the phosphorylated polysaccharide is subjected to chelate-bonding to calcium ions released during the dissolution or calcium atoms remaining on the apatite surface, so that the composition of the present invention is adsorbed to bones or teeth, and a curing reaction is progressed between the phosphorylated polysaccharide and a polyvalent metal salt so that bonding takes place. Further, the phosphate group of the phosphorylated polysaccharide is subjected to chelate-bonding to a metal or ceramics which are luting materials for the biological hard tissues, thereby showing adsorbability. Therefore, the phosphorylated polysaccharide is used as a bonding component of the adhesive composition for biological hard tissues having high biocompatibility.

The phosphorylated polysaccharide in the present invention includes, for example, lactose, sucrose, sucralose, cellobiose, trehalose, maltose, Palatinose (registered trademark), maltotriose, maltodextrin, cyclodextrin, glycosylsucrose, amylose, amylopectin, cycloamylose, glycogen, cellulose, agarose, cluster dextrin, mannan, pullulan, and the like, a part or all of hydroxyl groups of which are phosphorylated.

More specifically, the phosphorylated polysaccharide includes phosphorylated lactose, phosphorylated sucrose, phosphorylated sucralose, phosphorylated cellobiose, phosphorylated trehalose, phosphorylated maltose, phosphorylated Palatinose (registered trademark), phosphorylated maltotriose, phosphorylated maltodextrin, phosphorylated cyclodextrin, phosphorylated glycosylsucrose, phosphorylated amylose, phosphorylated amylopectin, phosphorylated cycloamylose, phosphorylated glycogen, phosphorylated cellulose, phosphorylated agarose, phosphorylated cluster dextrin, phosphorylated mannan, phosphorylated pullulan, and the like. These phosphorylated polysaccharides can be used alone or in a combination of two or more kinds. Among them, one or more members selected from the group consisting of phosphorylated maltodextrin, phosphorylated cyclodextrin, phosphorylated glycosylsucrose, phosphorylated amylose, phosphorylated amylopectin, phosphorylated cycloamylose, phosphorylated glycogen, phosphorylated cellulose, phosphorylated agarose, phosphorylated cluster dextrin, phosphorylated mannan, and phosphorylated pullulan are preferred, from the viewpoint of bonding to biological hard tissues, strength of the cured product, and production costs. The phosphorylated pullulan is more preferred, from the viewpoint of safety to the living body of the polysaccharides themselves, and their constituting units oligosaccharides and monosaccharides, and from the viewpoint of being less likely to be metabolized with amylase or the like orally, thereby making it less likely to serve as a nutrient for bacteria.

The phosphorylated polysaccharide can be produced according to a known method, including subjecting a hydroxyl group of the polysaccharide as mentioned above to phosphorylation. The method includes, for example, a method of reaction thereof with sodium metaphosphate described in *Carbohydrate Research* 302 (1997), 27-34, methods of reaction thereof with sodium phosphate described in Japanese Patent Laid-Open Nos. 2005-330269 and 2005-330270, and the like. Furthermore, as described in WO 87/07142, a method of reacting phosphorus pentoxide and pullulan to give phosphorylated pullulan is preferably used. The phosphorylated polysaccharide obtained can be subjected to IR spectroscopy, NMR spectroscopy, and the like, whereby the structure thereof can be confirmed. Here, a degree of phosphorylation of the phosphorylated polysaccharide can be adjusted in accordance with a known method by adjusting amounts of raw materials used, and reaction conditions, and the like.

In addition, a part of all of the above-mentioned phosphorylated polysaccharide (A) may be formed into salts, which are exemplified by and for example, sodium salts, potassium salts, calcium salts, magnesium salts, ammonium salts, and the like. The salts of the phosphorylated polysaccharide mentioned above can be prepared in accordance with a known method.

The number-average molecular weight (Mn) of the phosphorylated polysaccharide is preferably from 1,000 to 100,000, more preferably from 2,000 to 70,000, even more preferably from 5,000 to 50,000, even more preferably from 10,000 to 50,000, even more preferably from 10,000 to 40,000, and even more preferably from 10,000 to 30,000, from the viewpoint of bonding to the biological hard tissues, the strength of cured product and production costs. It is preferable that when the number-average molecular weight (Mn) of the phosphorylated polysaccharide is 1,000 or more, sufficient strength in the cured product and bonding strength are obtained, and that when the number-average molecular weight is 100,000 or less, it is free of risk of lowering solubility in a solvent, and the viscosity is not too high so that the operability is favorable. Here, in the present specification, the number-average molecular weight (Mn) of the phosphorylated polysaccharide can be measured in accordance with a method described in Examples set forth below.

It is desired that the phosphorylated polysaccharide is a polysaccharide in which hydroxyl groups are subjected to phosphorylation in an amount of preferably from 0.5 to 15% by number, and more preferably from 2 to 10% by number, of all the hydroxyl groups in one molecule. The proportion of the number of the hydroxyl groups subjected to phosphorylation in the phosphorylated polysaccharide can be calculated by measuring a phosphorus content by performing elemental analysis of the phosphorylated polysaccharide, and assuming that the measured phosphorus is entirely derived from that hydroxyl groups that are subjected to phosphorylation.

The polyvalent metal salt (B) in the present invention is used for the purposes of increasing the strength of cured product, the control of solubility, and the residuality. In other words, the polyvalent metal salt is utilized as a metal source for the purpose of increasing the strength of the cured product by forming a chelate bond with an unreacted phosphate group of the phosphorylated polysaccharide, during which the phosphorylated polysaccharide forms a chelate bond with calcium atoms remaining on the apatite surface of bones or teeth and calcium ions dissolved and released through a phosphate group, to cause a curing reaction therebetween, thereby exhibiting bonding property.

The polyvalent metal salt (B) is preferably a salt other than the phosphates of the polyvalent metal elements, and hydroxides, halides, and oxides of metal elements such as magnesium, calcium, strontium, barium, zinc, aluminum, and the like are preferably used. Specific examples include magnesium hydroxide, calcium hydroxide, aluminum chloride, calcium chloride, magnesium chloride, zinc chloride, aluminum acetate, aluminum nitrate, barium nitrate, calcium nitrate, magnesium nitrate, strontium nitrate, calcium fluoroborate, and the like. Among them, the halides and oxides are preferred, and calcium salts (halides and oxides) and barium oxide, magnesium oxide, and zinc oxide are more preferred, and calcium chloride is even more preferred. These polyvalent metal salts can be used alone or in a combination of two or more kinds. Here, in the present specification, the polyvalent metal salt other than the phosphates may be simply described as a polyvalent metal salt (B).

The polyvalent metal salt (B) can be used in the form in which the salt is dissolved or dispersed in a solvent, so that the shape thereof is not particularly limited. In addition, the average particle size thereof is preferably from 0.001 to 50 µm, and more preferably from 0.001 to 10 µm, from the viewpoint of handling property of the composition obtained and mechanical strength of a cured product and the like.

The polyvalent metal salt (B) is contained in an amount of preferably 0.1 parts by mass or more, and more preferably 1 part by mass or more, based on 100 parts by mass of the phosphorylated polysaccharide (A), from the viewpoint of an increasing effect of the mechanical strength of the cured product. Also, when the kit of the present invention is used in the form of a pasty cement, which is a preferred embodiment thereof, the polyvalent metal salt is contained in an amount of preferably 1,000 parts by mass or less, more preferably 200 parts by mass or less, and even more preferably 50 parts by mass or less, from the viewpoint of avoiding the deficiency of fluidity of the above-mentioned paste so as not to make it difficult to give sufficient supply to a restoration site of the biological hard tissues. From these viewpoints, the polyvalent metal salt (B) is contained in an amount of preferably from 0.1 to 1,000 parts by mass, more preferably from 1 to 200 parts by mass, and even more preferably from 1 to 50 parts by mass, based on 100 parts by mass of the phosphorylated polysaccharide (A).

The solvent (C) is used from the viewpoint of dissolving, swelling or dispersing a phosphorylated polysaccharide (A) and/or a polyvalent metal salt (B).

The solvent includes water, organic solvents, or a mixture thereof.

As the water, distilled water or ion-exchanged water is preferred, from the viewpoint of not containing impurities.

The water is contained in an amount of preferably 1 part by mass or more, more preferably 10 parts by mass or more, and even more preferably 20 parts by mass or more, based on 100 parts by mass of the phosphorylated polysaccharide (A), from the viewpoint of adsorbability of a phosphate group of the phosphorylated polysaccharide to hydroxyapatite. In addition, the water is contained in an amount of preferably 2,000 parts by mass or less, more preferably 1,000 parts by mass or less, and even more preferably 500 parts by mass or less, from the viewpoint of controlling the lowering of the concentration of a matrix component in order to favorably maintain the strength of a cured product and bonding strength. Therefore, the water is contained in an amount of preferably from 1 to 2,000 parts by mass, more preferably from 10 to 1000 parts by mass, and even more preferably from 20 to 500 parts by mass, based on 100 parts by mass of the phosphorylated polysaccharide (A).

The organic solvent includes methanol, ethanol, 1-propanol, 2-propanol, 1-butanol, 2-methyl-2-propanol, acetone, methyl ethyl ketone, tetrahydrofuran, diethyl ether, diisopropyl ether, hexane, toluene, chloroform, ethyl acetate, butyl acetate, and the like. These organic solvents can be used alone or in a combination of two or more kinds. Among them, when both the safety to a live body and the facilitation of removal based on volatile property are taken into consideration, a water-soluble organic solvent is preferred, and specifically, ethanol, 2-propanol, 2-methyl-2-propanol, acetone, and tetrahydrofuran are preferred. The amount of the organic solvent contained is not particularly limited, and in some cases the blending of the above-mentioned organic solvent would not be necessitated depending upon the embodiments. In an embodiment where an organic solvent is used, the organic solvent may be properly mixed with a given ratio with water, and the organic solvent can be contained in an amount of preferably from 1 to 2,000 parts by mass, based on 100 parts by mass of the entire amount of the water.

The kit for bonding to biological hard tissues of the present invention can further contain, in addition to the phosphorylated polysaccharide (A), a polyvalent metal salt (B) and a solvent (C), phosphoric acid, polyphosphoric acid, and/or salts thereof (D).

The phosphoric acid, polyphosphoric acid, and/or salts thereof (D) in the present invention exhibits an action of increasing the strength of the cured product of the composition obtained, and at the same time exhibits an action of increasing bonding strength to biological hard tissues such as bones and teeth, metals and ceramics. Specific mechanisms are considered to be the following. A phosphorylated polysaccharide (A) is subjected to chelate bonding to calcium atoms remaining on the apatite surface or calcium ions dissolved and released therein. On the other hand, the phosphoric acid, polyphosphoric acid, and/or salts thereof (D) have a lower molecular weight than the phosphorylated polysaccharide (A), so that the compounds have high motility and also a high phosphate group concentration within the molecule. Accordingly, it is considered that the phosphoric acid, polyphosphoric acid, and/or salts thereof (D) forms a chelate bonding to the phosphorylated polysaccharide (A) and unreacted calcium atoms and calcium ions, thereby increasing adsorption to the bones or teeth, which in turn progresses a subsequent curing reaction thereof, to improve bonding strength. From these aspects, it is considered that the phosphoric acid, polyphosphoric acid, and/or salts thereof (D) is a compound serving to complement a chelate reaction between the phosphorylated polysaccharide (A) and calcium atoms or calcium ions, thereby increasing the functions of the composition obtained.

The phosphoric acid is exemplified by a general phosphoric acid, and the salts of the phosphoric acid are exemplified by calcium phosphate, barium phosphate, magnesium phosphate, sodium phosphate, potassium phosphate, and the like. Among them, calcium phosphate is preferred for the following reasons.

Specifically, as mentioned above, the phosphate group of the calcium phosphate complements a chelate reaction between a phosphorylated polysaccharide (A) and calcium atoms or calcium ions, and at the same time the calcium atoms thereof forms a chelate bond with a phosphate group not chelate-bonded with bones or the like, among the phosphate groups of the phosphorylated polysaccharide (A), so that a network structure is formed between the phosphorylated polysaccharide (A) and the calcium phosphate, thereby forming a strong cured product. In addition, the calcium phosphate particles also act as a reinforcing material in the cured product, thereby giving an effect of imparting strength. On the other hand, phosphoric acid and calcium contained in calcium phosphate are constituting elements of inorganic components constituting bones or teeth, so that the calcium phosphate functions as an element supplying source in regeneration and restoration of biological hard tissues such as bones or teeth, in the adhesive composition for biological hard tissues.

The calcium phosphate may be a compound having $Ca^{2+}$ and $PO_4^{3-}$ as constituting elements, and specific examples include hydroxyapatite, apatite carbonate, calcium dihydrogenphosphate $[Ca(H_2PO_4)_2]$, calcium hydrogenphosphate $(CaHPO_4)$, α-TCP[α-tricalcium phosphate, $Ca_3(PO_4)_2$], β-TCP[β-tricalcium phosphate, $Ca_3(PO_4)_2$], OCP (octacalcium phosphate), tetracalcium phosphate, and hydrates thereof, and the like. These calcium phosphates can be used alone, or in a combination of two or more kinds.

In addition, when the calcium phosphate is considered as an element supplying source in the regeneration and restoration of biological hard tissues such as bones or teeth, it is preferable that the calcium phosphate does not contain an inhibitory substance such as carbonate ions, and specifically, a compound represented by the following formula (I):

$$Ca_xH_yO_z(PO_4)_l(OH)_m(H_2O)_n \quad (I)$$

wherein x and l are integers of 1 or more, and y, z, m and n are integers of 0 or more.

Among them, hydroxyapatite, calcium dihydrogenphosphate, calcium hydrogenphosphate, α-TCP, β-TCP and OCP are more preferred, from the viewpoint of reactivity with the phosphate group of the phosphorylated polysaccharide (A), hardening reinforcement of a cured product, and regeneration of the biological hard tissues in an even higher quality.

The shape of the calcium phosphate is not particularly limited. In addition, the average particle size of the calcium phosphate is preferably from 0.001 to 50 μm, and more preferably from 0.001 to 10 μm, from the viewpoint of handling property, mechanical strength after curing of the composition obtained, or the like.

On the other hand, the polyphosphoric acid includes linear polyphosphoric acid, obtained by dehydration condensation of ortho-phosphoric acid; cyclic phosphoric acid; polyphosphoric acids in which phosphoric acid is connected in an irregular form in a network manner. The linear polyphosphoric acid is exemplified by pyrophosphoric acid, tripolyphosphoric acid, tetrapolyphosphoric acid, pentapolyphosphoric acid, hexapolyphosphoric acid, and the like. The cyclic polyphosphoric acid is exemplified by trimetaphosphoric acid, tetrametaphosphoric acid, hexametaphosphoric acid, and the like. The polyphosphoric acid in which phosphoric acid is connected in an irregular form in a network manner is exemplified by ultrapolyphosphoric acid.

The salts of the polyphosphoric acid include alkali metal salts such as sodium salts and potassium salts; mixed salts of alkali metal ions and hydrogen ions; ammonium salts, and the like. Among them, the alkali metal salts of polyphosphoric acid is preferred, from the viewpoint of convenience in use.

Here, these phosphoric acid, polyphosphoric acid and/or salts thereof can be used alone or in combination of two or more kinds. Also, the phosphoric acid, polyphosphoric acid and/or salts thereof mentioned above can be prepared in accordance with a known method, and the salt compound may be partly or entirely in the form of a salt.

The calcium phosphate is contained in an amount of preferably 1% by mass or more, more preferably 10% by mass or more, and even more preferably substantially 100% by mass, of the phosphoric acid, polyphosphoric acid and/or salts thereof (D), from the viewpoint of adhesion of the composition and strength of a cured product thereof.

The content of the phosphoric acid, polyphosphoric acid and/or salts thereof (D) is not particularly limited, and the phosphoric acid, polyphosphoric acid and/or salts thereof is contained in an mount of preferably from 1 to 2,000 parts by mass, more preferably from 1 to 1,000 parts by mass, and even more preferably from 5 to 500 parts by mass, based on 100 parts by mass of the phosphorylated polysaccharide (A), from the viewpoint of adhesion of the composition and strength of the cured product. Here, the content of the phosphoric acid, polyphosphoric acid and/or salts thereof (D) means a total content of the phosphoric acid, polyphosphoric acid and salts thereof contained in the composition.

In addition, the kit for bonding to biological hard tissues of the present invention can further contain, in addition to those mentioned above, a filling material (E).

The filling material in the present invention is blended from the viewpoint of handling property of the composition obtained, mechanical strength after curing, and the like.

The filling material as mentioned above is not particularly limited, so long as the filling material is added to a composition used in medical applications, such as filling materials presently usable in a dental restorative composition or the like, and the filling material includes organic filling materials, inorganic filling materials, and organic-inorganic composite filling materials.

The materials for the organic filling materials include, for example, methyl polymethacrylate, ethyl polymethacrylate, methyl methacrylate-ethyl methacrylate copolymers, a crosslinked methyl polymethacrylate, a crosslinked ethyl polymethacrylate, polyamides, polyvinyl chloride, polystyrenes, chloroprene rubber, nitrile rubber, ethylene-vinyl acetate copolymers, styrene-butadiene copolymers, acrylonitrile-styrene copolymers, acrylonitrile-styrene-butadiene copolymers, and the like, and each of these organic filling materials can be used alone or in a mixture of two or more kinds.

The materials for inorganic filling materials include quartz, silica, alumina, silica-titania, silica-titania-barium oxide, silica-zirconia, silica-alumina, lanthanum glass, borosilicate glass, sodium glass, barium glass, strontium glass, glass ceramics, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, strontium calcium fluoroaluminosilicate glass, and the like. Each of these inorganic filling materials can be used alone or in a mixture of two or more kinds.

In order to adjust the fluidity of the composition, the above-mentioned inorganic filling material may be used after previously surface-treating with a known surface treatment agent such as a silane coupling agent as needed. The surface treatment agent includes, for example, methyltrichlorosilane, diphenyldichlorosilane, vinyltrimethoxysilane, vinyltriethoxysilane, vinyltrichlorosilane, vinyltri(β-methoxyethoxy) silane, γ-methacryloyloxypropyl trimethoxysilane, 11-methacryloyloxyundecyl trimethoxysilane, γ-glycidoxypropyl trimethoxysilane, γ-mercaptopropyl trimethoxysilane, γ-aminopropyl triethoxysilane, hexamethyldisilazane, and the like. Here, the surface treatment method is not particularly limited, and a known method can be used.

The organic-inorganic composite filling material refers to a filling material obtained by previously adding a monomer compound to the above-mentioned inorganic filling material to form into a paste-like state, polymerizing the components, and pulverizing the reaction mixture. As the organic-inorganic composite filling materials, for example, TMPT filling material (a product obtained by blending trimethylolpropane methacrylate and a silica filling material, and polymerizing the components, and pulverizing the reaction mixture) or the like can be used.

The filling material (E) is contained in an amount of preferably from 1 to 1,000 parts by mass, based on 100 parts by mass of the phosphorylated polysaccharide (A), from the viewpoint of adhesion of the composition and strength of the cured product.

In addition, the kit for bonding to biological hard tissues can further contain a biologically active agent (F), in addition☐ to those mentioned above.

The composition obtained from the kit of the present invention has excellent biological absorbability; therefore, when the composition contains a biologically active agent, the composition sequentially releases the biologically active agent, during which the above composition is absorbed to the live body according to an interaction between an ionic group such as phosphate group contained and a biologically active agent, or a sealing effect of the cured product (gel). Therefore, the composition obtainable with the kit of the present invention can function as a substrate for sustained-release of the above biologically active agent.

The biologically active agent is not particularly limited, and includes bone morphogenetic proteins, antibiotics, polynucleotides, carcinostatic agents, growth factors, vaccine and the like. The bone morphogenetic proteins are exemplified by BMP-2, BMP-3, BMP-3b, BMP-4, BMP-5, BMP-6, BMP-7, BMP-8, BMP-9, BMP-10, BMP-11, BMP-12, BMP-13, BMP-14, BMP-15, BMP-16, BMP-17, BMP-18 and the like.

In addition, the biologically active agent includes alkylating agents, platinum agents, metabolic antagonists, topoisomerase inhibitors, antitumor antibiotics, mitotic inhibitors, aromatase inhibitors, thymidylate synthase inhibitors, demineralized bone matrix, DNA antagonists, farnesyltransferase inhibitors, pump inhibitors, histone acetyltransferase inhibitors, metalloproteinase inhibitors, ribonucleoside reductase inhibitors, TNFα agonists, TNFα antagonists, endothelin A receptor antagonists, retinoic acid agonists, immunomodulators, hormone agents, antihormone agents, photodynamic agents, tyrosine kinase inhibitors, and the like.

The content of the biologically active agent (F) cannot be unconditionally determined because the content depends upon patients to which the kit of the present invention is applied, and the content can be properly adjusted.

Further, the kit for bonding to biological hard tissues of the present invention can contain a pH adjustment agent, an ultraviolet absorbent, a thickening agent, a colorant, a perfume or the like, within the range so that the effects of the present invention would not be hindered.

The kit for bonding to biological hard tissues of the present invention is not particularly limited, so long as the kit contains a phosphorylated polysaccharide (A), a polyvalent metal salt (B), and a solvent (C), and the kit can be easily prepared by a method known to one of ordinary skill in the art.

Specifically, the kit for bonding to biological hard issues of the present invention can be supplied in a pasty form prepared by previously blending a phosphorylated polysaccharide (A), a polyvalent metal salt (B), a solvent (C), and other ingredients as needed. In addition, the kit can be supplied in the form of a preparation dosage upon use by blending the above components in a clinical work site to make a pasty form.

In addition, since the phosphorylated polysaccharide (A) reacts with metal ions of the polyvalent metal salt (B), each of the phosphorylated polysaccharide (A) and the polyvalent metal salt (B) is stored in separate containers, from the viewpoint of storage stability. In other words, in an embodiment, the kit for bonding to biological hard tissues of the present invention is provided so that the kit contains a first agent containing at least a phosphorylated polysaccharide (A), and a second agent containing at least a polyvalent metal salt (B). Here, a solvent (C) can be contained in a first agent and/or a second agent, or the solvent may be provided in the form of a separate agent containing a solvent (C) alone.

In addition, even in a case where the kit further contains phosphoric acid, polyphosphoric acid, and/or salts thereof (D), since these components (D) react with metal ions of the polyvalent metal salt (B), it is preferable that the above components (D) are stored in a different container from a polyvalent metal salt (B). For example, the kit may be provided as a first agent containing a phosphorylated polysaccharide (A), a second agent containing at least a polyvalent metal salt (B), and a third agent containing at least phosphoric acid, polyphosphoric acid, and/or salts thereof (D), or a first agent containing a phosphorylated polysaccharide (A) may be blended with the phosphoric acid, polyphosphoric acid, and/or salts thereof (D) and supplied.

In a case where a biologically active agent (F) is contained, the form of the kit can be appropriately adjusted depending upon the physical properties.

A specific embodiment includes a kit containing a first agent in a powdery form, containing a phosphorylated polysaccharide (A) and a calcium phosphate (D); and a second at in a pasty form, containing a polyvalent metal salt (B) and a solvent (C), and it is preferable that a first agent and a second agent are kneaded to react immediately before use.

Thus, the adhesive composition for biological hard tissues obtained from the kit of the present invention has sufficiently high strength of the cured product that is hardened, and further has strong bonding property, so that the adhesive composition is suitably used in a medical material such as cement for bones or a dental cement. Those materials to which the adhesive composition for biological hard tissues obtained by the kit of the present invention shows strong bonding property include bones, tooth tissues, metals such as titanium and stainless steel, and ceramics.

Since the composition obtained from the kit of the present invention functions as a substrate for sustained release of a biologically active agent, the present invention also provides a kit prepared by further blending the kit for bonding to biological hard tissues of the present invention with a biologically active agent, in other words, a kit for sustained release of a biologically active agent in biological hard tissues, containing a phosphorylated polysaccharide, a polyvalent metal salt other than the phosphates, a biologically active agent, and a solvent. In addition, since the biologically active agent can be sustained-release, a kit for treatment of a disease in biological hard tissues, comprising a phosphorylated polysaccharide, a polyvalent metal salt other than the phosphates, a biologically active agent, and a solvent, in other words, a therapeutic agent, is provided.

In the present invention, the diseases in the biological hard tissues are not particularly limited so long as the diseases are diseases in bone tissues and dental tissues. The diseases are exemplified by, for example, osteosarcoma, Ewing sarcoma, osteochondrosarcoma, malignant fibrous histiocytoma, osteofibrosarcoma, metastatic osteosarcoma, myeloma, acute pyogenic osteomyelitis, chronic osteomyelitis, Brodie's abscess, pyogenic spondylitis, postoperative infections of artificial joint replacement, and the like. In addition, it is also expected that the therapeutic agent of the present invention is applied to the diseases that require an action for promoting bone restoration, for example, osteoporosis, bone defects after resection of benign or malignant osteosarcoma, bone defects after curettage of osteosarcoma-resembling diseases, bone defects after injury or fracture, bone defects of bone-collecting parts, bone defects parts during artificial joint replacement or the like.

The therapeutic agent of the present invention can contain components that are usable in the kit for bonding to biological hard tissues so long as the therapeutic agent contains the phosphorylated polysaccharide, the polyvalent metal salt other than the phosphates, the biologically active agent, and the solvent mentioned above, and the components are the same as the kit. Also the production method is also the same.

Since the therapeutic agent of the present invention is capable of control-releasing a biologically active agent, the therapeutic agent is used according to an appropriate method matching the sustain-release property, and the therapeutic agent can be used, for example, internally, externally, by an injection, or a topically filling, so long as the above-mentioned biologically active agent can be delivered to a site of disease in the biologically hard tissues. Specifically, the therapeutic agent can be directly topically administered or filled to a site with a disease in the biologically hard tissues, or the therapeutic agent can also be administered can be administered intravenously, intra-arterially, subcutaneously, intramuscularly, intraperitoneally, or the like, or the therapeutic agent may be administered or filled with an endoscope or the like. In addition, in a case of administering as an external preparation such as a suppository, the therapeutic agent may be administered in accordance with a suitable administration method. Here, the terms "administering, administered, administration" as used herein embrace administering, filling or detaining a therapeutic agent.

The amount used, the number of use and the use time period of the therapeutic agent of the present invention differ depending upon the kinds of the biologically active agent contained, and they are appropriately set according to preparation dosage form, a method of use, purpose of use, and age, body weight, symptoms of the patients to be administered, and not at certain levels.

The present invention also provides a composition for treating and/or preventing a disease in biologically hard tissues, the composition containing a kit for bonding to biological hard tissues of the present invention and further a biologically active agent. Moreover, the present invention provides a composition for treating and/or preventing a disease in biologically hard tissues, the composition containing a phosphorylated polysaccharide and a polyvalent metal salt other than the phosphates.

The present invention also provides a method of treating a disease in biological hard tissues, including the step of administering to a subject a composition containing a phosphorylated polysaccharide, a polyvalent metal salt other than the phosphates, a biologically active agent, and a solvent at a disease site in the biological hard tissues. Since the above composition control-releases a biologically active agent, the method of treatment of the present invention can exhibit an effect of performing treatments of a disease in biological hard tissues in a sustained manner. The subject is preferably human having a disease in biological hard tissues or human from whom a disease in biological hard tissues is prevented, or the subject may be a pet animal or the like.

EXAMPLES

The present invention will be described on the basis of Examples and Comparative Examples, without intending to restrict the present invention to those Examples and the like.

Production 1

Synthesis of Phosphorylated Pullulan

Using a separable flask having an inner volume of 2 L, 40.0 g of pullulan (manufactured by Hayashibara Co., Ltd.) was dissolved in 200 mL of distilled water at room temperature. While stirring this solution, 1,000 g of a 1 M aqueous phosphoric acid solution (of which pH of was adjusted to 5.5 with sodium hydroxide) was added thereto over 10 minutes, and after the addition, the mixture was continued stirring for an additional 1 hour. Thereafter, about 1,100 mL of distilled water was distilled away at a temperature between 100° C. and 103° C., subsequently the residue was continued stirring at 170° C. for 3 hours, and the reaction product was cooled to room temperature. The reaction product was taken out, and cooled to room temperature. The reaction product was taken out, and pulverized with a mortar, to give 98.4 g of a brown solid.

Ninety grams of the brown solid obtained above was dissolved in 1,500 mL of distilled water. While stirring this solution, 1,500 mL of a 99.5% ethanol was added thereto over 10 minutes. At the same time as the addition, the formation of the deposited products was confirmed. After the termination of addition, the stirring was continued for an additional hour. Thereafter, the mixture was allowed to stand to separate into layers, and the supernatant was removed by decantation method. Thereafter, the remaining precipitates were re-dissolved in 1,500 mL of distilled water, 1,500 mL of a 99.5% ethanol was added thereto over 10 minutes, and the precipitates were collected. The above procedures were carried out two more times, the precipitates were then dissolved in distilled water (400 mL), and the solution obtained was added in small amounts to a 99.5% ethanol (2,000 mL) over 5 minutes. The deposited precipitates were filtered with a Kiriyama filter (3G), washed with a 99.5% ethanol (500 mL), thereafter dried at 60° C. under a reduced pressure for 12 hours, to give 28.5 g of a white solid with a slightly brownish color. Further, 25 g of this white solid was dissolved in distilled water, and this solution was applied to a desktop electrodialyzer (Micro Acilyzer S3, manufactured by SANACTIS), to give 13 g of phosphorylated pullulan in the form of a pale brown solid with transparency.

The solid obtained was subjected to an IR spectroscopy (manufactured by Shimadzu Corporation, FTIR-8200PC) (KBr tablet method). As a result, peaks ascribed to phosphate group sites are observed at 1,000 to 1,200 cm$^{-1}$. In addition, $^{31}$P-NMR (manufactured by JEOL Ltd., JNM-LA500) was measured, and as a result, signals ascribed to phosphorus of the phosphoric acid moiety, ester-bonded to pullulan were obtained at 2 to 5 ppm. An elemental analysis for phosphorus atoms was conducted according to ICP emission spectroscopy (manufactured by Jarrell-Ash, IRIS-AP), and it was judged from the results that about 8.8% by number of the hydroxyl groups of the pullulan were subjected to phosphorylation. Furthermore, the GPC analysis (column: TSK gel α-M (manufactured by Tosoh Corporation), mobile phase: 0.1 M aqueous NaCl) was carried out. As a result, the solid had a number-average molecular weight (Mn) of 22,000.

Production Example 2

Synthesis of Phosphorylated Pullulan

A phosphorylated pullulan was produced in the same manner as in Production Example 1, to give a phosphorylated pullulan, in which about 7.2% by number of hydroxyl groups of the pullulan were subjected to phosphorylation, and a number-average molecular weight (Mn) was 32,000.

Production Example 3

Synthesis of Phosphorylated Pullulan

A phosphorylated pullulan was produced in the same manner as in Production Example 1, to give a phosphorylated pullulan, in which about 6.8% by number of hydroxyl groups of the pullulan were subjected to phosphorylation, and a number-average molecular weight (Mn) was 22,000.

Example 1

Preparation of Cement Composition

The amount 0.1 g of the phosphorylated pullulan synthesized in Production Example 1 was pulverized with a mortar, and a powder obtained was named a powder agent A. In 0.05 mL of distilled water was dissolved 0.005 g of calcium chloride, and an aqueous solution obtained was named a solution agent a. The powder agent A and the solution agent a were kneaded at room temperature to give a homogeneous paste or a pasty cement composition. Here, (A)/(B) was 100/5.

Example 2

Preparation of Cement Composition

The amount 0.1 g of the phosphorylated pullulan synthesized in Production Example 1 and 1 g of β-TCP (manufactured by TAIHEI CHEMICAL INDUSTRIAL CO., LTD.) as a calcium phosphate were pulverized with a mortar and mixed, and a powder obtained was named a powder agent B. The powder agent B and the solution agent a in Example 1 were kneaded at room temperature to give a homogeneous paste or a pasty cement composition. Here, (A)/(B)/(D) was 100/5/1000.

Example 3

Preparation of Cement Composition

The amount 0.1 g of the phosphorylated pullulan synthesized in Production Example 1, 0.25 g of α-TCP (manufactured by TAIHEI CHEMICAL INDUSTRIAL CO., LTD.), 0.25 g of β-TCP (manufactured by TAIHEI CHEMICAL INDUSTRIAL CO., LTD.), 0.25 g of hydroxyapatite (manufactured by TAIHEI CHEMICAL INDUSTRIAL CO., LTD.) and 0.25 g of DCPD (calcium hydrogenphosphate dihydrate, $CaHPO_4 \cdot 2H_2O$, manufactured by TAIHEI CHEMICAL INDUSTRIAL CO., LTD.) as calcium phosphates were pulverized with a mortar and mixed, and a powder obtained was named a powder agent C. The powder agent C and the solution agent a in Example 1 were kneaded at room temperature to give a homogeneous paste or a pasty cement composition. Here, (A)/(B)/(D) was 100/5/1000.

Comparative Example 1

Preparation of Cement Composition

The amount 0.1 g of pullulan (manufactured by Hayashibara Co., Ltd.) and the solution agent a in Example 1 were kneaded at room temperature to give a homogeneous paste or a pasty cement composition.

Evaluation 1

Evaluation on Bonding to Hydroxyapatite

Preparation of Samples for Evaluating Shear Bond

A plate made of hydroxyapatite as a member to be coated (diameter 13 mm×height 2 mm) (manufactured by PENTAX Corporation, APP601) was placed at a bottom of a mold having dimensions of diameter 25.4 mm×depth 10 mm, and an epoxy resin was poured thereinto. After curing the epoxy resin, the resin was taken out from the mold, to furnish a plate made of hydroxyapatite embedded into the epoxy resin for evaluation on bonding. The surface of the embedded plate made of hydroxyapatite and a separately furnished edge side of a cylindrical rod made of hydroxyapatite (diameter 5 mm×10 mm) were each polished under running water with a #1000 silicon carbide paper (manufactured by NIHON KENT CO., LTD.), and after the termination of polishing, the water on the surface was air-blown to dryness, to give a coated surface.

Next, the paste of Example 1 or Comparative Example 1 was heaped up at the edge side of the above-mentioned cylindrical rod made of hydroxyapatite, and the cylindrical rod made of hydroxyapatite was implanted so as to be in perpendicular to the plate made of hydroxyapatite. After implantation, an excess cement composition bleeding out to the surroundings of the cylindrical rod made of hydroxyapatite was removed with an instrument, and the cylindrical rod was allowed to stand at room temperature (25° C.) until the cement composition was cured. A total of five samples for bonding test were prepared, and all of the cured samples were allowed to stand in a thermostat held at 37° C. for 24 hours. Here, each of the pastes prepared immediately before use was used.

In addition, as to the cement compositions prepared in accordance of the methods of use attached to each of the manufactured articles using BIOPEX-R (manufactured by HOYA), a commercially available calcium phosphate-based cement as Reference Example 1, or a surgical simplex bone cement (manufactured by Howmedica Osteonics), a PMMA bone cement, as Reference Example 2, samples for bonding tests were prepared in the same manner as above.

Measurement of Shear Bond Strength

Figure 2:
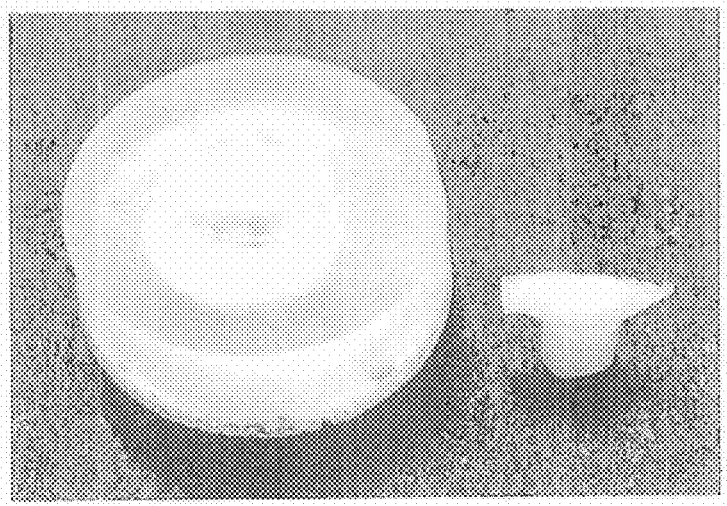
FIG. 2 is a view showing a shear cross section during the measurement of shear bond strength of Example 1. The left side is a plate made of hydroxyapatite, and the right side is a cylindrical rod made of hydroxyapatite.

The shear bond strength of the obtained five samples for bonding test was measured with a universal testing machine (manufactured by Instron) by setting a cross-head speed at 0.5 mm/minute, and an average was defined as shear bond strength of each composition to the hydroxyapatite. The results are shown in FIG. 1. Also, a cross section upon shearing of Example 1 is shown in FIG. 2. Here, upon the measurement with a universal tester, in all the test samples, when the cylindrical rod was detached from the coated plate by deadweight, shear bond strength was judged as being 0.00 MPa.

Evaluation 2

Evaluation of Bonding to Titanium

Measurement of Shear Bond Strength

The same procedures as in Evaluation 1 using the cement compositions of Example 1, Comparative Example 1, and Reference Examples 1 and 2 were carried out except that a member to be coated was changed to a plate made of titanium (10 mm×10 mm×3 mm), a cylindrical rod to be planted was changed to a cylindrical rod made of titanium (diameter 5 mm×height 5 mm) to measure shear bond strength to titanium. The results are shown in FIG. 1.

It can be seen from the results of FIG. 1 that the composition of the example has high bonding strength even after 24 hours of bonding. In addition, it can be seen from the results of FIG. 2 that breakage on the side of hydroxyapatite is recognized in the cross section upon shearing, so that the composition of the example has a high bonding strength.

Figure 3:
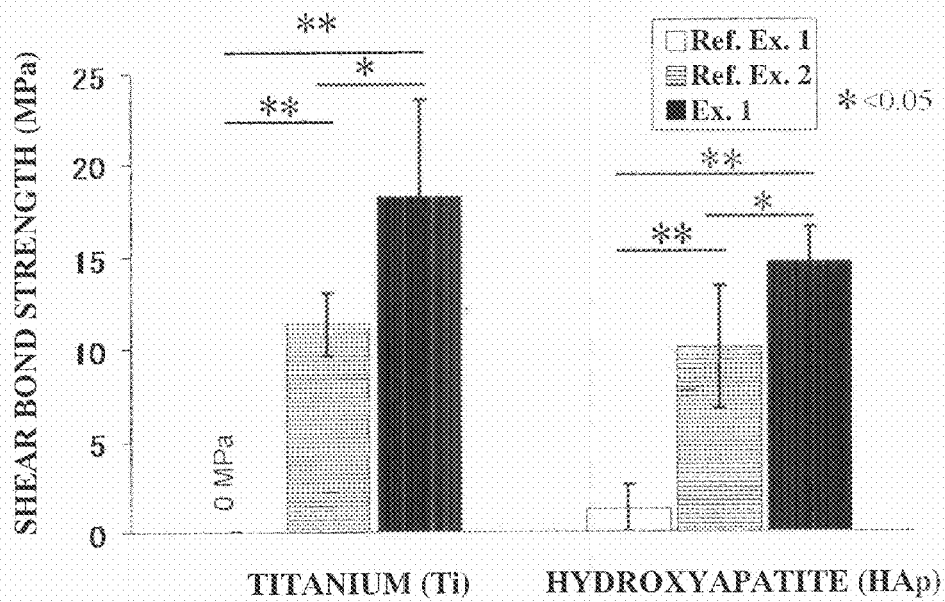
FIG. 3 is a graph showing the results of significance test for the shear bond strength of the compositions of Example 1 and Reference Examples 1 to 2.

In addition, as to the cement compositions of Example 1 and Reference Examples 1 and 2, five samples each for bonding test were further prepared in the same manner as in Evaluations 1 and 2 to measure shear bond strength to the titanium or hydroxyapatite. During the measurement, multiple comparative tests were conducted using Tukey method and Games-Howell method. The results are shown in FIG. 3. Here, in FIG. 3, "**" shows the groups that were judged to have significance at $p<0.05$ in both the Tukey method and the Games-Howell method, and "*" shows the groups that were judged to have significance at $p<0.05$ only in the Tukey method.

It can be seen from the results of FIG. 3 that the composition of Example 1 has significantly excellent bonding property as compared to the commercially available products of Reference Examples 1 and 2.

Evaluation 3

Evaluation on Bonding Between Hydroxyapatite and Stainless Steel

Preparation of Evaluation Samples of Shear Bond

A surface of a plate made of hydroxyapatite (sizes: diameter 13 mm×height 2 mm) (manufactured by PENTAX Corporation, APP601) as a member to be coated was polished with #1000 silicon carbide paper (manufactured by NIHON KENSHI CO., LTD.) under running water, and after the termination of polishing, the water on the surface was air-blown to dryness, to give a coated surface.

Next, the paste of Example 1 or Reference Examples 1 and 2 was heaped up at the edge side of the cylindrical rod made of stainless steel (sizes: diameter 7 mm×height 20 mm), and the cylindrical rod made of stainless steel was implanted so as to be in perpendicular to the plate made of hydroxyapatite. After implantation, an excess cement composition bleeding out to the surroundings of the cylindrical rod made of stainless steel was removed with an instrument, and the cylindrical rod was allowed to stand at room temperature (25° C.) until the cement composition was cured. A total of eight samples for bonding test were prepared, and all of the cured samples were allowed to stand in a thermostat held at 37° C. for 24 hours. Here, each of the pastes prepared immediately before use was used.

Measurement of Shear Bond Strength

The shear bond strength of the obtained eight samples for bonding test was measured in the same manner as in Evaluation 1, and evaluation was made.

As a result, the composition of Example 1 has shear bond strength of 2.95 MPa, and based on the matter that the breakage form is entirely interfacial breakage between the cement composition and the stainless steel surface, the cement composition of the present invention and stainless steel have shear bond strength of 2.95 MPa. On the other hand, in the compositions of Reference Examples 1 and 2, based on the matters that the stainless steel cylindrical rods were detached from the coated plate by their deadweights in all the samples for bonding test, and the breakage form was entirely an interfacial breakage between the cement composition and the stainless steel surface, the compositions of Reference Examples 1 and 2 were judged to have shear bond strength of 0.00 MPa. It can be seen from this matter that the composition of Example 1 also shows excellent bonding property to stainless steel, in addition to hydroxyapatite and titanium.

Evaluation 4

Evaluation of Compressive Strength

Each of the compositions of Examples 1 and 2 and Reference Example 1 was filled in a separable mold (diameter 4 mm×depth 8 mm) made of Teflon (registered trademark) placed on a smooth glass plate cautiously so as not to include any gases in the mold, and thereafter pressed with a smooth glass plate from a top part. Thereafter, the composition was kept in a thermostat kept at 37° C. for 1 week, and the top and bottom glass plates were removed therefrom, and a cylindrical-form cured product of the cement composition was taken out of the above mold. The compressive strength of the cylindrical-form cured product obtained was measured by applying a load at a rate of 0.5 mm/minute in a shaft direction of the cylindrical-form cured product with a universal testing machine (manufactured by Instron) (n=4).

As a result, it can be seen that the compressive strengths of the cured products of the cement compositions of Examples 1 and 2 and Reference Example 1 were 38.33 MPa, 66.93 MPa, and 21.50 MPa, respectively, so that the composition of the example gives the cured product excellent strength.

Evaluation 5

Pulp-Capping Test of Dental Pulp

Figure 4:
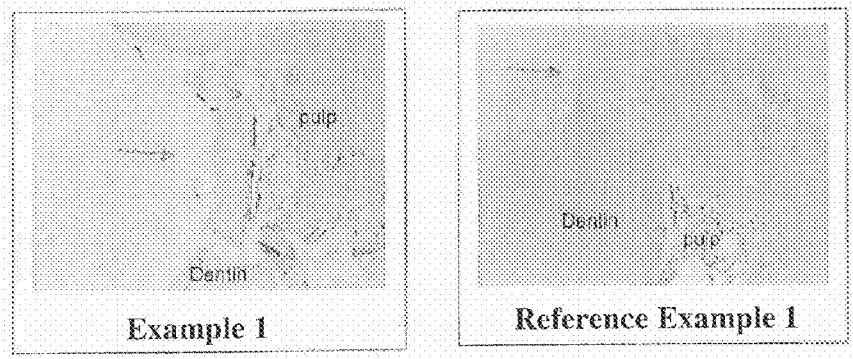
FIG. 4 is a view showing HE-stained optical microscopic sections of the maxillary first molar tooth. The left side is a representative section of a group subjected to pulp capping with the composition of Example 1, and the right side is that of a group subjected to pulp capping with the composition of Reference Example 3, wherein an arrow in each figure shows the portion subjected to pulp capping with the composition.

Using 8-week old male Wister rats as experimental animals, a mesial occlusion of the maxillary first molar tooth was carefully exposed while pouring sterile distilled water, with a ¼ diamond bar and a ½ stainless steel round bar. The exposed side was alternately washed with 6% NaOCl and 3% $H_2O_2$, the dental pulp was then directly subjected to pulp capping with the cement composition of Example 1 to fill an air gap part with CLEARFIL MegaBond (manufactured by Kuraray Medical Inc., a dental adhesive for filling cavity), CLEARFIL Protect Liner F (manufactured by Kuraray Medical Inc., a composite resin for filling cavity), and the restoration was completed. After two weeks of observation period, the rats were subjected to perfusion fixation with a 4% paraformaldehyde solution under intraperitoneal anesthesia to excise the first molar tooth, and the excised sample was then decalcified with a 10% EDTA solution, and subjected to a paraffin treatment according to an ordinary method to prepare continuous section specimen. The sections were subjected to hematoxylin-eosin staining (HE staining), and the stained sections were observed under an optical microscope. Representative results are shown in FIG. 4. Here, as Reference Example 3, a mixture of blending and kneading calcium hydroxide and sterile water was also evaluated in the same manner, and the number of tested specimens (n) was 5.

From the left side of FIG. 4, in a case where the composition of Example 1 was used, the formation of restored enamel is remarkable, forming nearly perfectly so as to cover the exposed pulp side. Here, the thickness of the formed amount was uneven. In addition, the dental pulp tissue morphologies were normal, and inflammatory cell infiltration was not observed. On the other hand, from the right side of FIG. 4, in a case where the composition of Reference Example 3 was used, although the dental pulp tissue morphologies were normal, the formation of restored enamel was also uneven in this case. It is deduced from this matter that the composition of Example 1 is bonded to the dental pulp to be absorbed, whereby the composition is replaced with dentin.

Figure 5:
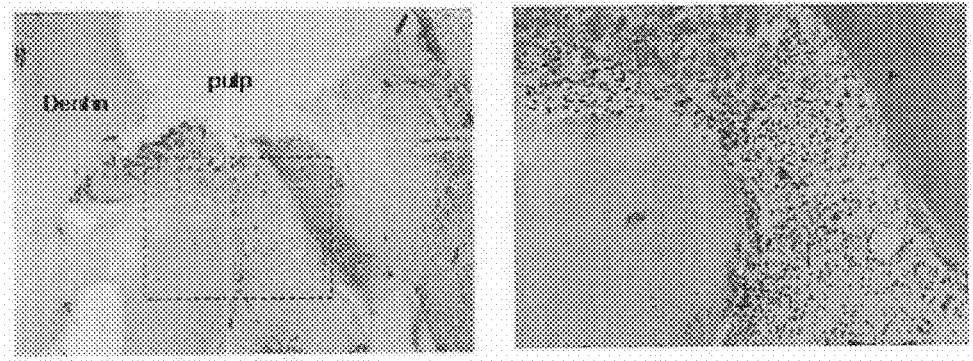
FIG. 5 is a view showing HE-stained optical microscopic sections of the maxillary first molar tooth. The left side is a representative section of a group subjected to pulp capping and filled with the composition of Example 1, and the right side is an enlarged view of the region inscribed with a frame in the left side figure.
Figure 6:
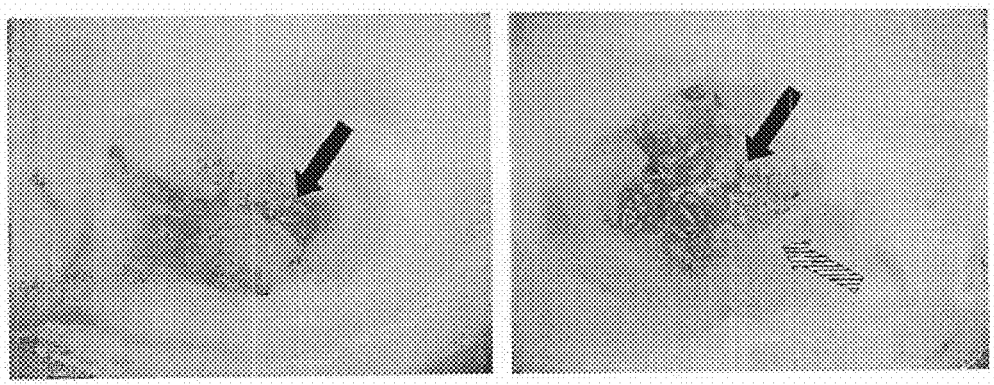
FIG. 6 is a view showing a photograph of a surface taken after two months from filling a cavity of the maxillary first molar tooth. The left side is a representative photograph of a group subjected to pulp capping and filled with the composition of Example 1, and the right side is a representative photograph of a group subjected to pulp capping with the composition of Example 1, and then filled with a commercially available resin, wherein an arrow (black solid) in each figure shows the residual part of the composition, and an arrow (with stripes) shows the residual part of the commercially available resin.

In addition, a pulp-capping test was conducted only using the composition of Example 1. More specifically, using 8-week-old male Wister rats as experimental animals, the maxillary first molar tooth was subjected to exposure and washing in the same manner as above, and the dental pulp was then directly subjected to pulp-capping with the cement composition of Example 1 to fill a gap part with the same composition to complete restoration. After one week of an observation period, the first molar tooth was excised to prepare a section specimen, the excised section was subjected to HE staining, and the stained section was observed under an optical microscope. Representative results are shown in FIG. 5. In addition, in a different rat, after two months of an observation period, the first molar tooth was excised, and the excised tooth was immersed and stored in a fixation solution for 12 days, in the same manner as above. As the fixation solution, a solution prepared by mixing 20 g of paraformaldehyde, 250 mL of distilled water, and 250 mL of a 0.1 M phosphate buffer was used. A photograph of the molar tooth surface after immersion in the fixation solution is shown in FIG. 6. Here, as a comparison, the evaluation was made in the same manner for one obtained by directly subjecting dental pulp to pulp-capping with the cement composition of Example 1, and filling a gap part with Evadyne Plus (manufactured by NEO DENTAL CHEMICAL PRODUCTS CO., LTD., a composite resin for filling cavity) to complete restoration, and the number of tested specimens (n) of each group was 3.

From the results of the stained sections, in a case where the pulp-capping and filling were carried out only with the composition of Example 1, it was confirmed that an exposed side was covered with a recovered enamel, so that the cavity was completely sealed (FIG. 5, left side). In addition, the right side of FIG. 5 shows an enlarged view of the boundary parts of the sites filled with the composition and teeth (dentin), and from the matter of not being able to find aberrancy in the teeth even after one week passed, it is deduced that the composition of Example 1 has excellent biocompatibility and also excellent bonding. Here, as to a case where the cavity was sealed with Evadyne Plus, the Evadyne Plus was found to be exfoliated upon the preparation of the specimen for optical microscopic observation, but it was confirmed that at least a coating was formed on the exposed pulp with the composition of Example 1 (not illustrated in the figure).

It was confirmed from FIG. 6 that in a case where pulp-capping and filling were carried out only with the composition of Example 1, it was confirmed that the composition of Example 1 remained in the cavity of the molar tooth (FIG. 6, left side). On the other hand, in a case where the dental pulp was pulp-capped with the composition of Example 1, and then filled with Evadyne Plus, the Evadyne Plus only remained in a slight amount even though that the composition of Example 1 was confirmed to remain in the cavity of the molar tooth, so that it is deduced that Evadyne Plus was easily exfoliated from the cavity (FIG. 6, right).

Evaluation 6

Injection Test to Femur

Using 8-week old male C57/bl6 mice as experimental animals, the functional evaluation of the cement composition of Example 1 or Example 3 was conducted in compliance with the Femoral Intramedullary Injection Model (Zilber S et. al, *J. Biomed Mater Res Part B: Appl Biomater.* 2008). Specifically, bone tunnel was made in the femoral intramedulla with an injection needle from mouse distal femur under general anesthesia, and a cement composition of Example 1, Example 2 (β-TCP-containing composition) or Example 3 (DCPD-containing composition) was injected, and the histological evaluations were carried out 2 weeks and 8 weeks after the injection for the composition of Example 1; 2 weeks, 5 weeks, and 8 weeks after the injection for the composition of Example 2; and 8 weeks after the injection for the composition of Example 3, respectively. The results using the composition of Example 1 are shown in FIG. 7, the results using the composition of Example 2 are shown in FIG. 8, and the results using the composition of Example 3 are shown in FIG. 9.

Figure 7:
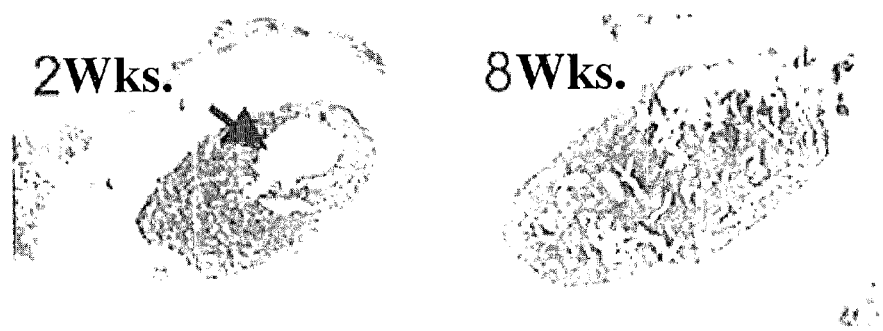
FIG. 7 is a view showing HE-stained optical microscopic sections of the femur injected with the composition of Example 1. The left side is a section after 2 weeks of injection, and the right side is that after 8 weeks of injection, wherein an arrow in the left side figure shows the site at which the composition is injected.

From FIG. 7, left side, in the femoral shaft at 2 weeks after the injection, the injected cement composition was exfoliated upon the preparation of the sections used in the histological evaluation, so that the part is observed as a cavity (arrow part), but the necrosis of the surrounding bone marrow or the like is not found so that it is observed that the cement composition and the bone marrow are closely bonding to each other, and it was found that the cement composition had a high compatibility to the bone marrow tissues.

It can be seen from FIG. 7, right side that the cavity of the part into which the cement composition is injected observed after 2 weeks disappears, and bone marrow tissues are regenerated in its place in the femoral shaft at 8 weeks after the injection. It was suggested from this finding that the cement composition of the present invention has bio-absorbability, and bone regeneration takes place in a site at which the cement composition was injected.

Figure 8:
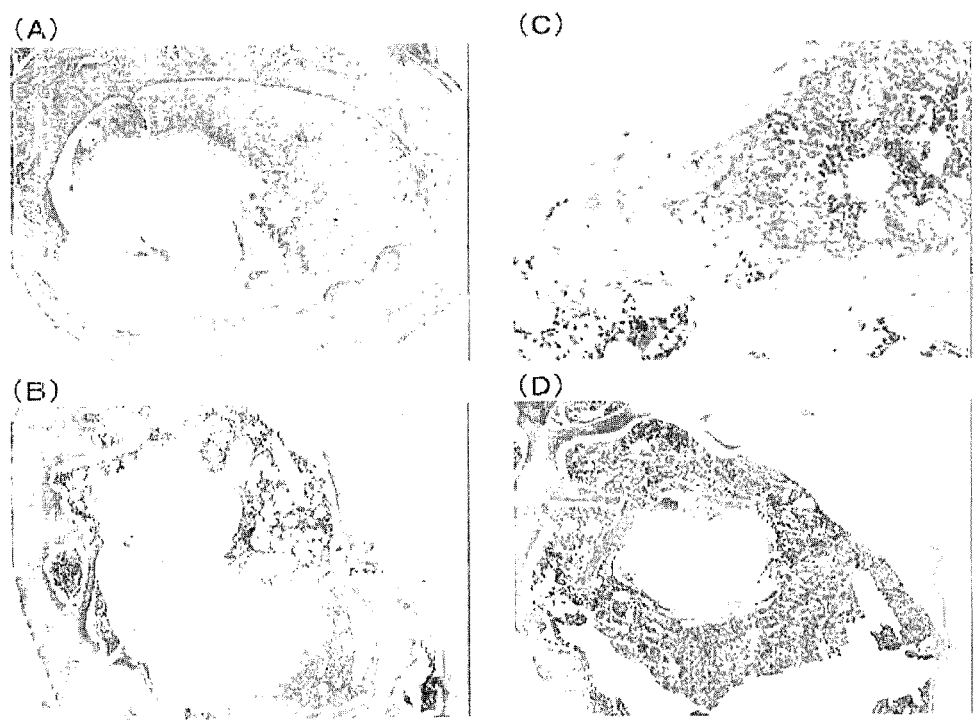
FIG. 8 is a view showing HE-stained optical microscopic sections of the femur injected with the composition of Example 2. (A) is a section after 2 weeks of injection, (B) is a section after 5 weeks of injection, (C) is an enlarged view of (B), and (D) is a section after 8 weeks of injection.
Figure 9:
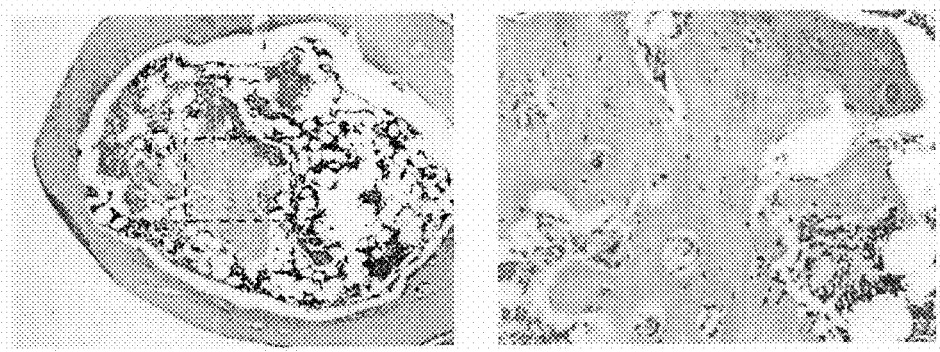
FIG. 9 is a view showing HE-stained optical microscopic sections of the femur injected with the composition of Example 3. The left side is a section after 8 weeks of injection, and the right side is an enlarged view of the region inscribed with a frame in the left side figure.

From FIG. 8, at 2 weeks after the injection, the cement composition of Example 2 injected is found in the bone marrow (FIG. 8A). At 5 weeks after the injection, even though the injected cement composition remains in the normal bone marrow, an image of ossifying from the surrounding edge thereof is observed (FIG. 8B). FIG. 8C is an enlarged view of the boundary part of the bone marrow and the cement composition of FIG. 8B, and it is evident that the newly generated bone tissues are contacted with the cement composition, so that bone regeneration takes place from the surrounding edge thereof. In addition, a large number of nuclei are observed in the newly generated bone tissues. At 8 weeks after the injection, an image of ossifying from the surrounding edge of the cement composition is observed in the same manner as that of 5 weeks after the injection, but the injected substance still remains in an internal thereof, so that it can be seen that the ossification is not completed to the internal part at this point (FIG. 8D).

In addition, in a case where the cement composition of Example 3 was used, at 8 weeks after the injection, the cement composition remaining in the normal bone marrow is not confirmed (FIG. 9, left side). Also, it can be seen from the enlarged photograph that the cement was completely absorbed in the femoral shaft, and replaced with normal bone tissues (FIG. 9, right side). It is suggested from these results that the biological absorption rate of the composition can be adjusted by modifying the kinds and amounts of the component (D) contained in the composition.

Evaluation 7

Pharmacological Test 1

The same procedures as in Example 1 were carried out except that a 0.1 g of a mixture prepared by mixing 40 g of the phosphorylated pullulan synthesized in Production Example 1 with a carcinostatic agent "Methotrexate" (manufactured by Takeda Pharmaceutical Co., Ltd.) in an amount of 0 g, 2 g, or 5 g, respectively, was used in place of 0.1 g of the phosphorylated pullulan of Production Example 1 in Example 1, to give a cement composition. The resulting cement composition was molded into a cylindrical shape having a diameter of 6 mm and a height of 2 mm. $1 \times 10^6$ Tumor cells (MNNG/HOS) were subcutaneously transplanted to the back of nude mice (BALB/cnu/nu), and allowed to stand for 7 to 10 days. After the tumor size grew to a size of 5 mm×5 mm, the above-mentioned molded product prepared was implanted immediately below the tumor. The tumor size was measured every 24 hours, to observe a change in volume of the tumors (diameter of major axis×diameter of minor axis×diameter of minor axis×0.5). Assuming that the tumor volume on the day of implantation of the cement composition was 100%, a volume increase of the tumor tissues was examined. The results are shown in FIG. 10.

Figure 10:
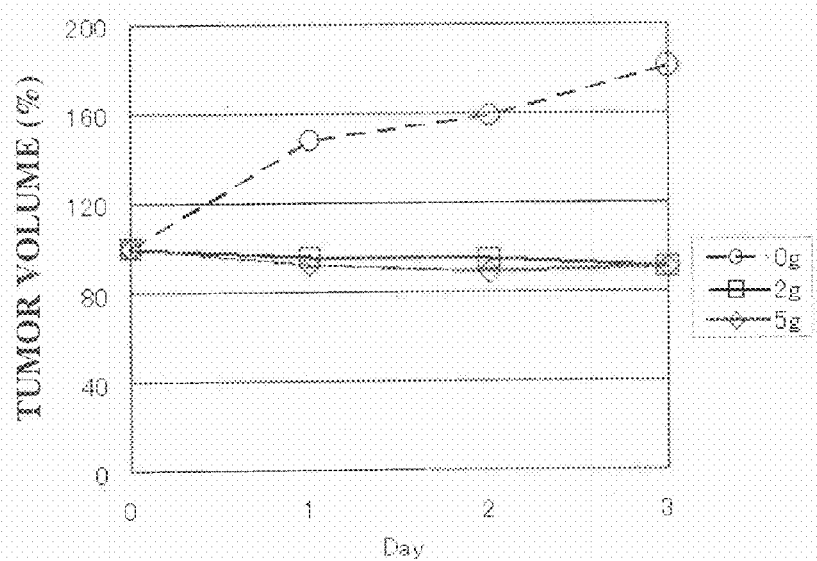
FIG. 10 is a graph showing suppression of proliferation of tumor tissues by a carcinostatic agent using the composition of Example 1.

From FIG. 10, proliferative suppression of the tumor tissues was observed in the composition blended with 2 g or 5 g of a carcinostatic agent. This shows that the carcinostatic agent is eluted from the composition of the present invention. Here, the proliferative suppression effects of the tumors of the molded product containing 2 g or 5 g of a carcinostatic agent are of the same level, and this is considered to be due to the fact that the amount of release of the carcinostatic agent (amount per time) from the molded product is of the same level.

Evaluation 8

Pharmacological Test 2

Four-week-old female C57/bl6 mice (wild-type) were intraperitoneally administered with 50 mg/kg pentobarbital, and anesthetized. Thereafter, the mice were subjected to median abdominal incision to excise ovaries on both sides, to prepare osteoporotic model mice.

Next, one week after the ovary excision, the right knee part was incised under anesthesia in the same manner as above, to open a distal end of the right femur. The pulp chamber was curetted using a 24-gauge injection needle from the same part over to the proximal femur. Subsequently, 20 µL of a cement composition having the following components was administered into the pulp chamber using a 25-gauge injection needle. Here, as a comparative control, a non-administered group (3) was also set. The tests were conducted at n=3.

(1) Calcium Hydrogenphosphate Dihydrate, hereinafter DCPD Group (200 µg of the phosphorylated pullulan synthesized in Production Example 1, 200 µg of DCPD, and 400 µL of a 31% aqueous calcium chloride solution)

(2) BMP Group (400 µg of the phosphorylated pullulan synthesized in Production Example 1, 100 ng of rhBMP-2, and 400 µL of a 31% aqueous calcium chloride solution)

(3) Non-Treated Group

Figure 11:
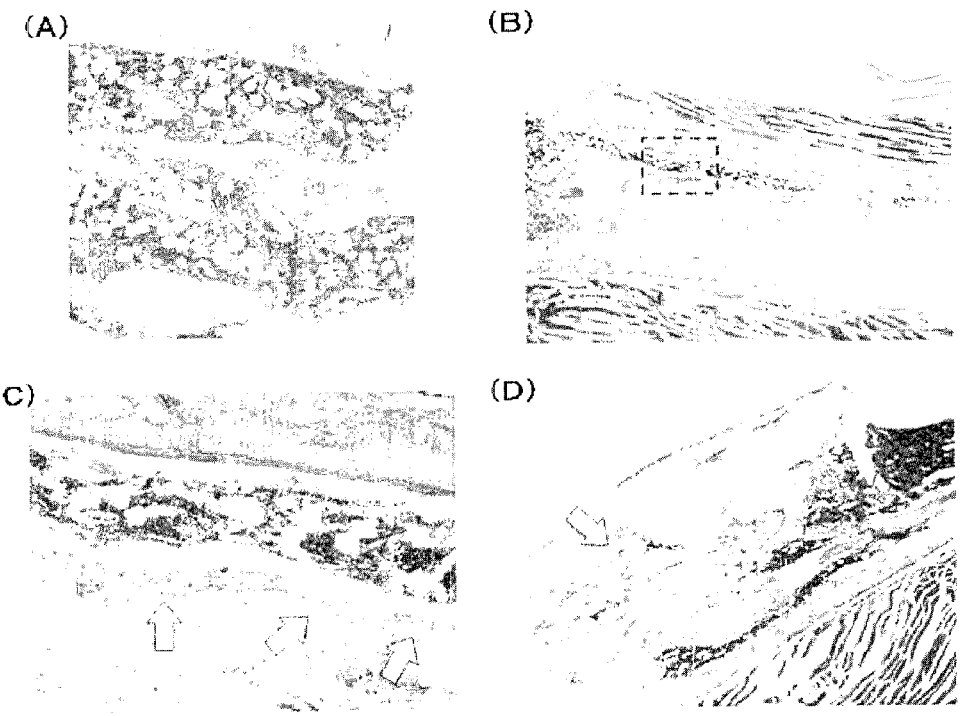
FIG. 11 is a view showing HE-stained optical microscopic sections of the femur of an osteoporotic model mouse injected with a phosphorylated pullulan-containing composition. (A) is a section of a non-treated group (4 weeks), (B) is a section of a DCPD group (8 weeks), (C) is an enlarged view of the region inscribed with a frame in (B), and (D) is a section of a BMP group (4 weeks). An arrow in the figure shows the site in which ossification is recognized.
Figure 12:
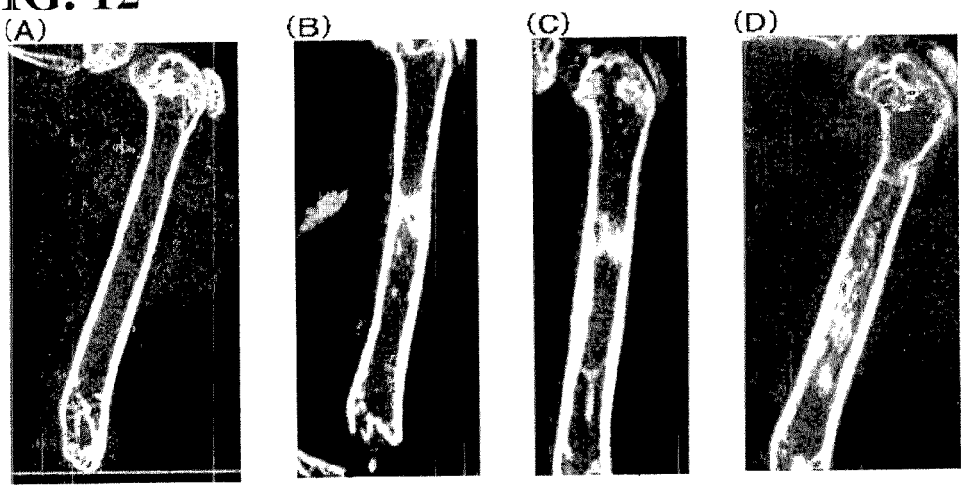
FIG. 12 is a view showing μCT image of the femur of an osteoporotic model mouse injected with a phosphorylated pullulan-containing composition. (A) is an image of a non-treated group (4 weeks), (B) is an image of DCPD group (4 weeks), (C) an image of a BMP group (4 weeks), and (D) is an image of a BMP group (8 weeks).

For each of Groups, mice were sacrificed after 4 weeks or 8 weeks from the administration to the femur, and the pathohistological evaluation (HE staining) and the radiological evaluation (µCT 48 µm/slice) were made therewith. The results of HE staining are shown in FIG. 11, and the results of µCT are shown in FIG. 12.

From FIG. 11A, in the Non-Treated Group, lipomeningocele is present in the bone marrow, and ossification could not be found even in µCT (FIG. 12A). From FIGS. 11B and C, in the DCPD Group, newly generated bone is confirmed to be formed in the surrounding of the injected cement, so that it can be seen that the bone can be formed even when suffering from osteoporosis by administering a phosphorylated pullulan-containing composition. Also, in the BMP Group, ossification of the tissues is found at one month after the injection (FIG. 11D), and it can be seen from FIGS. 12C and D that bone regeneration with the passage of time is found, so that BMP activity in the cement is maintained. From this finding, it is suggested that the phosphorylated pullulan-containing composition can serve as an excellent carrier for BMP because the composition does not generate polymerization heat.

Evaluation 9

Pharmacological Test 3

Four-week-old female BALB/c nude mice were intraperitoneally administered with pentobarbital at 50 mg/kg, and anesthetized. Thereafter, the right knee part was incised, to open a distal end of the right femur. Next, the pulp chamber was curetted using a 24-gauge injection needle from the same part over to the proximal femur. Thereafter, a mixture prepared by mixing $1 \times 10^6$ human osteosarcoma cells (HOS/MNNG) with 20 µL of Matrigel was administered with a 25-gauge injection needle into the above pulp chamber, to prepare osteosarcoma model mice.

Next, after one week from transplantation of the osteosarcoma cells, the right knee part was incised under anesthesia in the same manner as above to open a distal end of the right femur. The pulp chamber was curetted using a 24-gauge injection needle from the same part over to the proximal femur. Subsequently, 20 µL of a cement composition having the following components was administered into the pulp chamber using a 25-gauge injection needle.

(1) 400 µg of the phosphorylated pullulan synthesized in Production Example 1, 10 mg of Methotrexate (MTX), 400 µL of a 31% aqueous calcium chloride solution On the third day after the administration of the cement, the mice were sacrificed, and the pathohistological evaluation (HE staining) was carried out therewith. The results are shown in FIG. 13.

Figure 13:
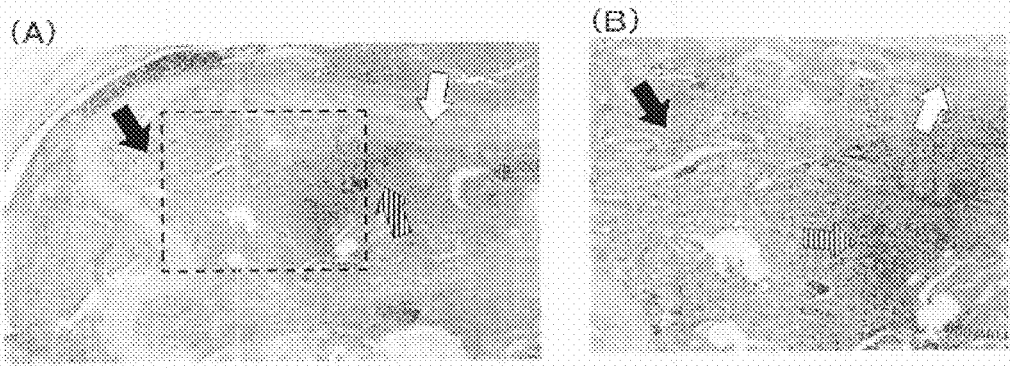
FIG. 13 is a view showing HE-stained optical microscopic sections of the femur of an osteocarcinoma model mouse injected with a phosphorylated pullulan-containing composition. (A) is a section after 3 days of injection, (B) is an enlarged view of the region inscribed with a frame in the left side figure, wherein in each figure an arrow (open) shows a residual site of the composition, an arrow (black solid) a residual site of tumor cells, and an arrow (with stripes) a necrosis site of tumor cells.

It can be seen from FIG. 13 that tumor cells undergo necrosis in the surroundings of the cement. From this finding, it is suggested that a carcinostatic agent is released with the absorption of the phosphorylated pullulan-containing composition.

Evaluation 10

Evaluation 1 of Sustained-Release Property of Agent

A mixture prepared by mixing 0.4 g of the phosphorylated pullulan synthesized in Production Example 2 and 0.01 g of a bactericidal agent "Vancomycin Hydrochloride" (manufactured by Shionogi & Co., Ltd.) was mixed with a proper amount of a 31% aqueous calcium chloride solution (about 200 μL), and the mixture was allowed to cure into a cylindrical form (diameter: 6 mm, thickness: 2 mm) using a template (PP2). In addition, a mixture of 40 g of a poly (methyl methacrylate) cement (PMMA cement, Surgical Simplex P Radiopaque Bone Cement; Howmedica Inc., Limerick, Ireland) and 1 g of "Vancomycin Hydrochloride" was allowed to cure into a cylindrical form (diameter: 6 mm, thickness: 2 mm) (PMMA). Each of the cured products obtained was immersed in 500 μL of a 0.01 M phosphate buffered physiological saline, and the phosphate buffered aqueous solution was exchanged at 37° C. every 24 hours. The procedures were repeated until the phosphorylated pullulan was completely dissolved, and the Vancomycin (VCM) concentration in the collected solution was measured using enzyme immunoassay method (EIA method). The results are shown in FIG. 14.

Figure 14:
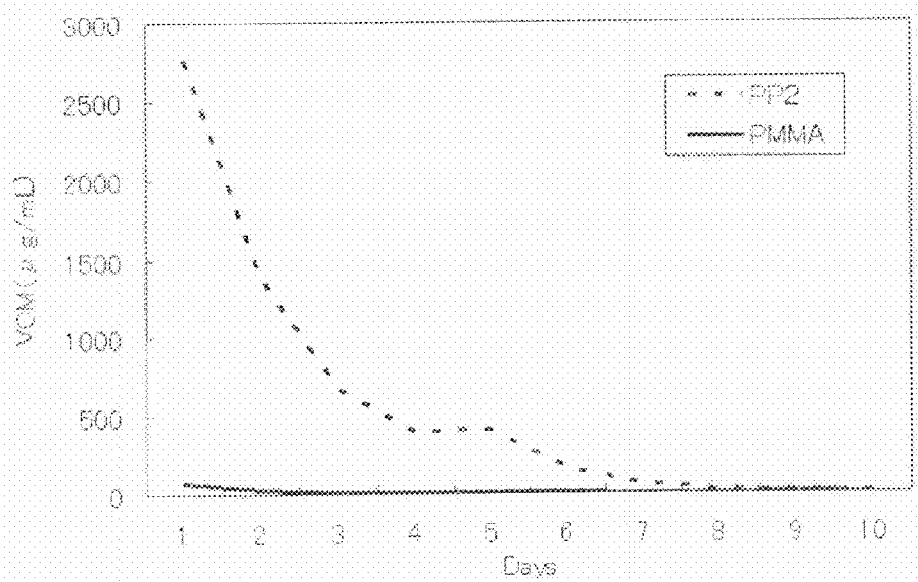
FIG. 14 is a graph showing an effused behavior of vancomycin (VCM) from a cured product using phosphorylated pullulan (PP2) synthesized in Production Example 2, and a cured product of poly(methyl methacrylate) cement (PMMA).

From FIG. 14, the VCM effusion from the PMMA cured product was the largest on the first day (72.4±10.8 μg/mL), and gradually lowered thereafter. On the other hand, the effusion from the phosphorylated pullulan cured product was also largest on the first day (2757.8±88.8 μg/mL), and gradually lowered thereafter, but the VCM concentration in the solution was significantly higher than that of the PMMA cured product until the eighth day.

Evaluation 11

Evaluation 2 of Sustained-Release Property of Agent

A mixture of 0.4 g of the phosphorylated pullulan synthesized in Production Example 2 or 3 and 0.02 g of a carcinostatic agent "Methotrexate" (manufactured by Pfizer) was mixed with a proper amount of a 31% aqueous calcium chloride solution (about 200 μL), and the mixture was allowed to cure into a cylindrical form (diameter: 6 mm, thickness: 2 mm) using a template (PP2, PP3) in the same manner as above. In addition, a mixture of 0.4 g of the PMMA cement used in Evaluation 10 and 0.02 g of "Methotrexate" was allowed to cure into a cylindrical form (diameter: 6 mm, thickness: 2 mm) (PMMA). Each of the cured products obtained was immersed in 500 μL of a 0.01 M phosphate buffered physiological saline, and the phosphate buffered aqueous solution was exchanged at 37° C. every 24 hours. The procedures were repeated until the phosphorylated pullulan was completely dissolved, and the Methotrexate (MTX) concentration in the collected solution was measured using enzyme immunoassay method (EIA method). The results are shown in FIG. 15.

Figure 15:
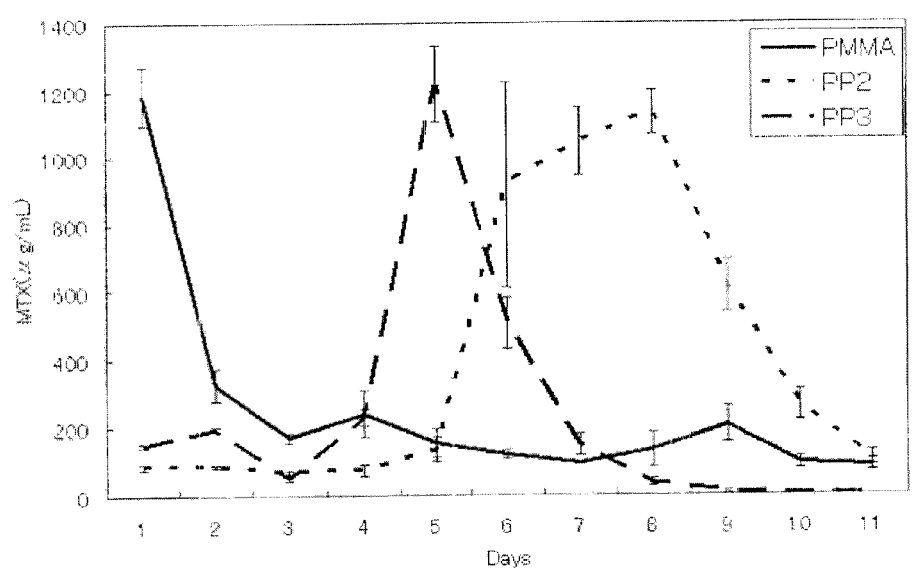
FIG. 15 is a graph showing an effused behavior of Methotrexate (MTX) from cured products of phosphorylated pullulans (PP) and a cured product of poly(methyl methacrylate) cement (PMMA). PP2 is a cured product using a phosphorylated pullulan synthesized in Production Example 2, and PP3 is a cured product using a phosphorylated pullulan synthesized in Production Example 3.

From FIG. 15, the MTX effusion from the PMMA cured product was the largest on the first day, drastically lowered on the second day, and maintained effusion at low concentrations thereafter. The MTX effusion from the cured product using the phosphorylated pullulan of Production Example 2 (PP2) showed effusion at low concentrations up to the fifth day, at an increasing concentration from the sixth day, and at high concentrations up to the tenth day. The MTX effusion from the cured product using the phosphorylated pullulan of Production Example 3 (PP3) showed effusion at low concentrations up to the fourth day, a sudden increase in the concentration on the fifth day, and again at low concentrations on the seventh day and on.

It was clarified from the above that the releasing behaviors from the composition differ depending upon the agents. This is deduced to be due to the interactions between the agent and an ionic group, for example, a phosphate group, contained in the composition. In addition, the releasing behaviors differ by having different phosphorylation percentages, whereby it is suggested that it is possible to control the release patterns by adjusting the phosphorylation percentage.

INDUSTRIAL APPLICABILITY

The adhesive composition for biological hard tissues provided by the kit for bonding to biological hard tissues is, for example, suitably used in for medical uses, such as cement for bones or dental cement. In addition, since the adhesive composition has excellent bio-absorbability, it is useful as fusion materials for artificial joint prosthesis, fusion materials for spine fracture, fusion materials for extremity fracture, filling materials for bone tumors in the region of orthopedics, filling materials and restorative materials at dental caries-defective sites, luting materials for prosthetic restorative materials such as inlay and crown, pulp-capping and lining materials, implant surface treatment materials, periodontal disease therapeutic materials, hyperesthesia preventive materials, dental pulp capping materials, substrates for DDS, substrates for systems engineering, and tissue bonding materials in the dental region.

The invention claimed is:

1. A method of treating a disease in biological hard tissues, the method comprising:
   administering an effective amount of a composition for treating the disease in biological hard tissues to the biological hard tissues of a subject in need thereof,
   wherein the biological hard tissues is at least one selected from the group consisting of bones, teeth, and tissue containing bones and teeth,
   wherein the composition comprises:
      (1) a phosphorylated polysaccharide,
      (2) a polyvalent metal salt other than phosphate,
      (3) a solvent, and
      (4) optionally, at least one component selected from the group consisting of phosphoric acid, polyphosphoric acid, a salt of the phosphoric acid, and a salt of polyphosphoric acid,
   wherein the composition contains the phosphorylated polysaccharide and a polyvalent metal salt other than phosphates stored separately which, when combined prior to use, form a paste, and wherein an amount of the polyvalent metal salt other than phosphate is from 1 to 1,000 parts by mass, based on 100 parts by mass of the phosphorylated polysaccharide, wherein the disease is at least one selected from the group consisting of osteosarcoma, Ewing sarcoma, osteochondrosarcoma, malignant fibrous histiocytoma, osteofibrosarcoma, metastatic osteosarcoma, myeloma, acute pyogenic osteomyelitis, chronic osteomyelitis, Brodie's abscess, pyogenic spondylitis, postoperative infections of artificial joint replacement, osteoporosis, bone defects after resection of benign or malignant osteosarcoma, bone defects after curettage of osteosarcoma, Ewing sarcoma, osteochondrosarcoma, malignant fibrous histiocytoma, osteofibrosarcoma, metastatic osteosarcoma, and myeloma, bone defects after injury or fracture, bone defects of bone-collecting parts, and bone defects during artificial joint replacement.

2. The method according to claim 1, wherein the phosphorylated polysaccharide is phosphorylated pullulan.

3. The method according to claim 1, wherein the polyvalent metal salt is at least one member selected from the group consisting of a halide and oxide of at least one polyvalent metal.

4. The method according to claim 3, wherein the halide is chloride.

5. The method according to claim 1, comprising phosphoric acid, polyphosphoric acid, and/or a salt thereof.

6. The method according to claim 5, comprising the salt of phosphoric acid, wherein the salt is a calcium phosphate.

7. The method according to claim 6, wherein the calcium phosphate is at least one calcium phosphate represented by the formula (I):

$$Ca_xH_yO_z(PO_4)_l(OH)_m(H_2O)_n \quad (I),$$

wherein x and l are integers of 1 or more, and y, z, m, and n are integers of 0 or more.

8. The method according to claim 7, wherein the calcium phosphate is at least one selected from the group consisting of hydroxyapatite, calcium dihydrogenphosphate, calcium hydrogenphosphate, α-tricalcium phosphate (α-TCP), β-tricalcium phosphate (β-TCP), and octacalcium phosphate (OCP).

9. The method according to claim 1, further comprising a filling material.

10. The method according to claim 1, wherein the polyvalent metal salt other than phosphate is in the form of particles having an average size of 0.001-50 μm.

11. The method according to claim 1, wherein a phosphorylation number of the phosphorylated polysaccharide is form 0.5 to 15%.

12. The method according to claim 1, wherein the solvent comprises water, an organic solvent, or a mixture thereof.

13. The method according to claim 1, wherein the solvent contains 100 parts by mass of water and from 1 to 2,000 parts by mass of an organic solvent.

14. A method for filling and repairing bone-defective and bone-gapped sites, the method comprising:

applying a restoration material composition to a site in need of repairing a bone-defect and/or bone-gap, wherein the restoration material composition provides adhesion or fusion between biological hard tissues and/or a biological hard tissue and a metal or ceramic, wherein the restoration material composition shows adhesion to the biological hard tissue, metals, and ceramics, wherein the biological hard tissues is at least one selected from the group consisting of bones, teeth, and tissue containing bones and teeth, wherein the restoration material composition comprises:
 (1) a phosphorylated polysaccharide,
 (2) a polyvalent metal salt other than phosphate,
 (3) a solvent, and
 (4) optionally, at least one component selected from the group consisting of phosphoric acid, polyphosphoric acid, a salt of the phosphoric acid, and a salt of polyphosphoric acid, wherein the restoration material composition contains the phosphorylated polysaccharide and a polyvalent metal salt other than phosphates stored separately which, when combined prior to use, form a paste, and wherein an amount of the polyvalent metal salt other than phosphate is from 1 to 1,000 parts by mass, based on 100 parts by mass of the phosphorylated polysaccharide.

15. The method according to claim 14, wherein the phosphorylated polysaccharide is phosphorylated pullulan.

16. The method according to claim 14, wherein the polyvalent metal salt is at least one member selected from the group consisting of a halide and oxide of at least one polyvalent metal.

17. The method according to claim 14, comprising phosphoric acid, polyphosphoric acid, and/or a salt thereof.

18. The method according to claim 17, comprising the salt of phosphoric acid, wherein the salt is a calcium phosphate represented by the formula (I):

$$Ca_xH_yO_z(PO_4)_l(OH)_m(H_2O)_n \quad (I),$$

wherein x and l are integers of 1 or more, and y, z, m, and n are integers of 0 or more.

19. The method according to claim 14, wherein the polyvalent metal salt other than phosphate is in the form of particles having an average size of 0.001-50 μm.

20. The method according to claim 14, wherein the site in need of repairing a bone-defect and/or bone-gap is at least one site selected form the group consisting of a site of an artificial joint prosthesis, a spine fracture, an extremity fracture, a site of a bone tumor, a dental caries-defective site, a site of an inlay and crown, a site of pulp-capping and lining, a site of an implant surface, a site of a periodontal disease, a site of hyperesthesia, and a dental restoration and dental bonding site.

* * * * *